US012703844B2

(12) United States Patent
Li et al.

(10) Patent No.: US 12,703,844 B2
(45) Date of Patent: Aug. 11, 2026

(54) CULTURE VESSELS CONTAINING 3D CELL CULTURE SUBSTRATES WITH DIFFUSION STRUCTURES

(71) Applicant: CORNING INCORPORATED, Corning, NY (US)

(72) Inventors: Feng Li, Shrewsbury, MA (US); Gregory Roger Martin, Acton, ME (US)

(73) Assignee: CORNING INCORPORATED, Corning, NY (US)

( * ) Notice: Subject to any disclaimer, the term of this patent is extended or adjusted under 35 U.S.C. 154(b) by 670 days.

(21) Appl. No.: 18/028,403

(22) PCT Filed: Sep. 29, 2021

(86) PCT No.: PCT/US2021/052546
§ 371 (c)(1),
(2) Date: Mar. 24, 2023

(87) PCT Pub. No.: WO2022/072421
PCT Pub. Date: Apr. 7, 2022

(65) Prior Publication Data

US 2023/0357688 A1 Nov. 9, 2023

Related U.S. Application Data

(60) Provisional application No. 63/085,701, filed on Sep. 30, 2020.

(51) Int. Cl.
*C12M 1/32* (2006.01)
*C12M 1/12* (2006.01)
*C12M 3/00* (2006.01)

(52) U.S. Cl.
CPC ............ *C12M 23/12* (2013.01); *C12M 21/08* (2013.01); *C12M 25/10* (2013.01); *C12M 25/14* (2013.01)

(58) Field of Classification Search
CPC .............................. C12M 23/12; C12M 25/14
See application file for complete search history.

(56) References Cited

U.S. PATENT DOCUMENTS 9,034,571 B2 5/2015 Berry et al.
9,701,938 B2 7/2017 Vukasinovic
(Continued)

FOREIGN PATENT DOCUMENTS

EP 2822612 A4 8/2015
EP 3653696 A1 5/2020
(Continued)

OTHER PUBLICATIONS

Hirschhaeuser F., et al., "Multicellular tumor spheroids: An underestimated tool is catching up again", J Biotechnol., Jul. 1, 2010, vol. 148, No. 1, pp. 3-15.

(Continued)

*Primary Examiner* — Jonathan M Hurst
(74) *Attorney, Agent, or Firm* — Chandra J Duncan

(57) ABSTRACT

A cell culture device comprises a multi-well cell culture plate comprising a plurality of wells, each well comprising a top, a bottom, and a sidewall disposed between the top and the bottom and having an interior surface comprising an ultra-low attachment surface. A plurality of scaffolds are disposed within wells of the multi-well cell culture plate, each scaffold comprising a cell-adherent surface. In some embodiments, the scaffold comprises a fiber scaffold. In some embodiments, the scaffold comprises an artificial vascular scaffold. In some embodiments, cell culture devices comprise a plurality of hydrogel scaffolds disposed in a multi-well cell culture plate, the plurality of hydrogel scaffolds comprising hydrogel fibers of differing lengths,
(Continued)

wherein opposite ends of a hydrogel fiber are disposed in different wells within the multi-well cell culture plate to create interconnected wells.

20 Claims, 8 Drawing Sheets

(56) References Cited

U.S. PATENT DOCUMENTS

| | | | |
|---|---|---|---|
| 2003/0113813 | A1 | 6/2003 | Heidaran et al. |
| 2014/0322806 | A1 | 10/2014 | Bennett et al. |
| 2016/0282338 | A1 | 9/2016 | Radisic et al. |
| 2020/0199541 | A1 | 6/2020 | Penninger et al. |
| 2020/0392453 | A1 | 12/2020 | Bennett et al. |

FOREIGN PATENT DOCUMENTS

| | | | |
|---|---|---|---|
| JP | 2005-526489 | A | 9/2005 |
| JP | 2016-536014 | A | 11/2016 |
| JP | 2019-162134 | A | 9/2019 |
| JP | 2020-523027 | A | 8/2020 |
| WO | 97/03182 | A1 | 1/1997 |
| WO | 2013/134383 | A1 | 9/2013 |
| WO | 2018/144860 | A1 | 8/2018 |
| WO | 2019/104069 | A1 | 5/2019 |

OTHER PUBLICATIONS

International Search Report and Written Opinion of the International Searching Authority; PCT/US2021/052546; dated Feb. 9, 2022; p. 10; European Patent Office.

OrganoPlate® Graft by Mimetas, Retreived from: https://mimetas.com/page/organoplate-graft?gclid=EAIaIQobChMInq3x0Y-75gIVBleGCh2M2wzPEAAYASAAEgKfE_D_BWE, Retreived on: May 11, 2023.

Pham M., et al., "Generation of human vascularized brain organoids Neuroreport", May 2, 2018, vol. 29, No. 7, pp. 588-593.

Sergei Grebenyuk et al., "Engineering organoid vasclarization", Frontiers in Bioengineering and Biotechnology, 2019, vol. 9, Article39, pp. 1-12.

Japanese Patent Application No. 2023-519861, Office Action dated Oct. 29, 2025, 7 pages (English Translation only), Japanese Patent Office.

CULTURE VESSELS CONTAINING 3D CELL CULTURE SUBSTRATES WITH DIFFUSION STRUCTURES

CROSS-REFERENCE TO RELATED APPLICATIONS

This is a national stage application under 35 U.S.C. § 371 of International Application No. PCT/US2021/052546, filed Sep. 29, 2021, which claims the benefit of priority under 35 U.S.C. § 119 of U.S. Provisional Application Ser. No. 63/085,701 filed on Sep. 30, 2020, the content of which are relied upon and incorporated herein by reference in their entirety.

TECHNICAL FIELD

The present specification generally relates to cell culture devices and, more specifically, to devices having diffusion structures for cell culture of spheroids.

BACKGROUND

Cells cultured in three dimensions, such as spheroids, can exhibit more in vivo-like functionality than their counterparts cultured in two dimensions as monolayers. In 2D cell culture systems, cells can attach to the substrate on which they are cultured. However, when cells are grown in 3D, such as within spheroids, the cells tend to interact with each other rather than attaching to the substrate. As such, cells cultured in 3D more closely resemble in vivo tissue in terms of cellular communication and the development of extracellular matrices.

3D cell aggregates or spheroids can be generated from normal cells, cancer cells, and cell lines. However, due to the lack of functional vascular structure in currently available culture devices, spheroid growth is restricted, which negatively impacts the inner cells within the spheroid. Compared to the outer cells on the spheroid, the inner cell mass has uneven nutrient and oxygen supply. Likewise, due to increased diffusional resistance out of the spheroid, waste products of cellular metabolism build up by the inner cells in the spheroid. These issues lead to the formation of necrotic cores, which have been reported in tumor spheroid culture when the size of spheroids reach to approximately 500 μm in diameter. Therefore, a need exists for culture devices that eliminate these restrictions.

SUMMARY

Embodiments of the disclosure as set forth herein provide cell culture devices that allow for spheroid growth. To reduce or eliminate restrictions for spheroid growth, and to establish a more tissue-like 3D culture, devices described herein introduce diffusion structures into the 3D cell cultures within wells of the culture device. The diffusion structures include scaffolds. In embodiments, the scaffolds comprise fibers. Nonlimiting examples of fibers include plastic or polymer fibers and hydrogel fibers. The fibers may be porous, gas permeable, or a combination thereof, to allow for nutrient supply and waste exchange in and out of the inner mass of a 3D culture through a passive diffusion mode of action.

In some embodiments, the culture substrates of the present disclosure are configured such that they provide improved and/or tailorable properties, including: improved cell distribution throughout the cross-sectional volume of the well, improved cell viability, improved waste removal from cells by operation of gravity towards the bottom of the cell, reduced necrotic cores, or other attributes, as compared to the culture vessels without such scaffolds as described herein.

In an aspect, a cell culture device comprises a multi-well cell culture plate comprising a plurality of wells, each well comprising a top, a bottom, and a sidewall disposed between the top and the bottom and having an interior surface comprising an ultra-low attachment surface; and a plurality of scaffolds disposed within wells of the multi-well cell culture plate, each scaffold comprising a cell-adherent surface.

In some embodiments, the bottom comprises a hemispherical shape.

In some embodiments, a scaffold is disposed in each well. In some embodiments, at least one end of the scaffold is anchored to a bottom portion of each well.

In some embodiments, the bottom comprises a plurality of microcavities. In some embodiments, a scaffold is disposed in each microcavity of the plurality of microcavities. In some embodiments, the scaffold is anchored to a bottom portion of each microcavity.

In some embodiments, the scaffold has a length of about 100 μm to about 3000 μm. In some embodiments, the scaffold has a length of about 100 μm to about 1000 μm. In some embodiments, the scaffold has a length of about 100 μm to about 500 μm. In embodiments, the scaffold has a length of at least 100 μm, at least 200 μm, at least 300 μm, at least 400 μm, at least 500 μm. In embodiments, the scaffold has a length not greater than 3000 μm, not greater than 2000 μm, not greater than 1000 μm, not greater than 500 μm.

In some embodiments, the scaffold has a width of about 10 μm to about 100 μm. In some embodiments, the scaffold has a width of about 10 μm to about 50 μm. In some embodiments, the scaffold has a width of about 10 μm to about 20 μm. In embodiments, the scaffold has a width of at least 10 μm, at least 15 μm, at least 20 μm. In embodiments, the scaffold has a width not greater than 100 μm, not greater than 50 μm, not greater than 20 μm.

In some embodiments, the scaffold comprises a fiber scaffold. In some embodiments, the fiber scaffold is formed from polyvinylalcohol, polyacrylamide, polyvinylpyrrolidone, poly(2-hydroxyethyl methacrylate), polystyrene, polypropylene, or polygalacturonic acid (PGA or pectin). In embodiments where PGA is used, attached 3D cell cultures may be released or harvested from the scaffold. For example, an enzyme and/or chelating agent, such as pectinase, may be used to digest the scaffold. In some embodiments, other hydrogels may be used that allow gentle digestion of the scaffold to release the 3D cell cultures.

In some embodiments, the fiber scaffold comprises a plurality of plastic fibers or polymer fibers. In some embodiments, each fiber in the plurality of plastic fibers is anchored to a bottom portion of each well. In some embodiments, individual fibers are distanced about 100 μm to about 200 μm apart from one another in each well.

In some embodiments, the scaffold comprises an artificial vascular scaffold.

In some embodiments, the artificial vascular scaffold comprises a hollow fiber. In some embodiments, the artificial vascular scaffold comprises a plurality of hollow fibers. In some embodiments, individual hollow fibers are anchored about 100 μm to about 200 μm from one another. In some embodiments, the hollow fiber is formed from a non-ionic polymer. In some embodiments, the non-ionic polymer comprises polyvinylalcohol, polyacrylamide, polyvinylpyrrolidone, poly(2-hydroxyethyl methacrylate), polystyrene, or polypropylene.

In some embodiments, the hollow fiber further comprises a hydrogel coating. In some embodiments, the artificial vascular scaffold comprises a hydrogel. In some embodiments, the hydrogel comprises extracellular matrix (ECM) proteins, decellularized tissue ECM scaffolds, crosslinked polymers, or a combination thereof. Non-limiting examples of adherent hydrogels comprise ECM proteins and decellularized tissue ECM scaffolds, and ECM examples include polysaccharide glycosaminoglycans (GAGs) and proteins such as collagens, laminins, and fibronectin. Non-limiting examples of non-adherent hydrogels comprise crosslinked polymers such as polyethylene oxide, polyvinyl alcohol, polyvinyl pyrrolidone, and polyacrylamide, among others.

In an aspect, a method of culturing three-dimensional (3D) cell cultures is provided. The method comprises seeding cells in a cell culture device according to one or more embodiments, as set out herein, wherein the cells attach to the cell adherent surface of the scaffold disposed within the cell culture device; and culturing the cells into a 3D cell culture by adding cell culture medium to the cell culture device to provide nutrients and oxygen, wherein the cells remain attached to the scaffold during addition or exchange of cell culture medium. In some embodiments, the method further comprises imaging 3D cell cultures attached to the scaffolds of the cell culture device.

In an aspect, an interconnected cell culture device comprises a multi-well cell culture plate comprising a plurality of wells, each well comprising a top, a bottom, and a sidewall disposed between the top and the bottom and having an interior surface comprising an ultra-low attachment surface; and a plurality of hydrogel scaffolds disposed in the multi-well cell culture plate, the plurality of hydrogel scaffolds comprising hydrogel fibers of differing lengths, wherein opposite ends of a hydrogel fiber are disposed in different wells within the multi-well cell culture plate to create interconnected wells.

In some embodiments, the bottom comprises a hemispherical shape.

In some embodiments, the hydrogel fibers have lengths in a range of about 100 μm to about 100 mm. In some embodiments, the hydrogel fibers have widths of about 10 μm.

In some embodiments, each hydrogel fiber comprises a cell-adherent surface. In some embodiments, the hydrogel fiber is formed from a non-attachment hydrogel and comprises a surface functionalized with attachment groups. Non-limiting examples of attachment groups include ECM proteins and attachment peptide sequences, such as arginylglycylaspartic acid (RGD). In some embodiments, the hydrogel fibers are formed of ECM proteins, decellularized tissue ECM scaffolds, ECM peptide sequences, and crosslinked polymers. Non-limiting examples of adherent hydrogels comprise ECM proteins and decellularized tissue ECM scaffolds. ECM examples include polysaccharide glycosaminoglycans (GAGs) and proteins such as collagens, laminins, and fibronectin. Non-limiting examples of non-adherent hydrogels comprise crosslinked polymers such as polyethylene oxide, polyvinyl alcohol, polyvinyl pyrrolidone, polyacrylamide, and polygalacturonic acid (PGA), among others.

In some embodiments, the hydrogel scaffolds are unanchored or free-floating within the wells.

In some embodiments, the bottom comprises a plurality of microcavities. In some embodiments, opposite ends of hydrogel fibers are disposed in different microcavities to create interconnected microcavities.

In an aspect, a method of forming an interconnected cell culture device is provided. The method comprises seeding a cell culture device with cells, the cell culture device comprising a multi-well cell culture plate comprising a plurality of wells, each well comprising a top, a bottom, and a sidewall disposed between the top and the bottom and having an interior surface comprising an ultra-low attachment surface; seeding the cell culture device with a plurality of hydrogel scaffolds, the hydrogel scaffolds comprising a plurality of hydrogel fibers, wherein opposite ends of a hydrogel fiber are disposed in different wells within the multi-well cell culture plate to create interconnected wells; and providing cell culture medium to provide nutrients and oxygen for cell growth and formation of three-dimensional (3D) cell cultures.

In some embodiments, the bottom comprises a hemispherical shape. In some embodiments, the bottom comprises a plurality of microcavities.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments and are incorporated into and constitute a part of this specification. The drawings illustrate the various embodiments described herein, and together with the description, serve to explain the principles and operations of the claimed subject matter.

BRIEF DESCRIPTION OF THE DRAWINGS

FIG. 4A shows a multi-well microplate, FIG. 4B shows a single well of the multi-well microplate, and FIG. 4C shows an exploded view of the area shown in box C of FIG. 4B, each according to one or more embodiments of the present disclosure.

DETAILED DESCRIPTION

Conventional devices and vessels for cell culture of spheroids suffer from drawbacks associated with the restricted growth of spheroids. Conventional devices lack a functional vascular structure, which negatively impacts the inner cells within the spheroid and restricts the spheroid growth. Compared to the outer cells on the spheroid, the inner cell mass has uneven nutrient and oxygen supply. Waste products of cellular metabolism build up by the inner cells in the spheroid, due to increased diffusional resistance out of the spheroid. These issues lead to the formation of necrotic cores, which have been reported in tumor spheroid culture when the size of spheroids reach to approximately 500 μm in diameter.

Figure 1:
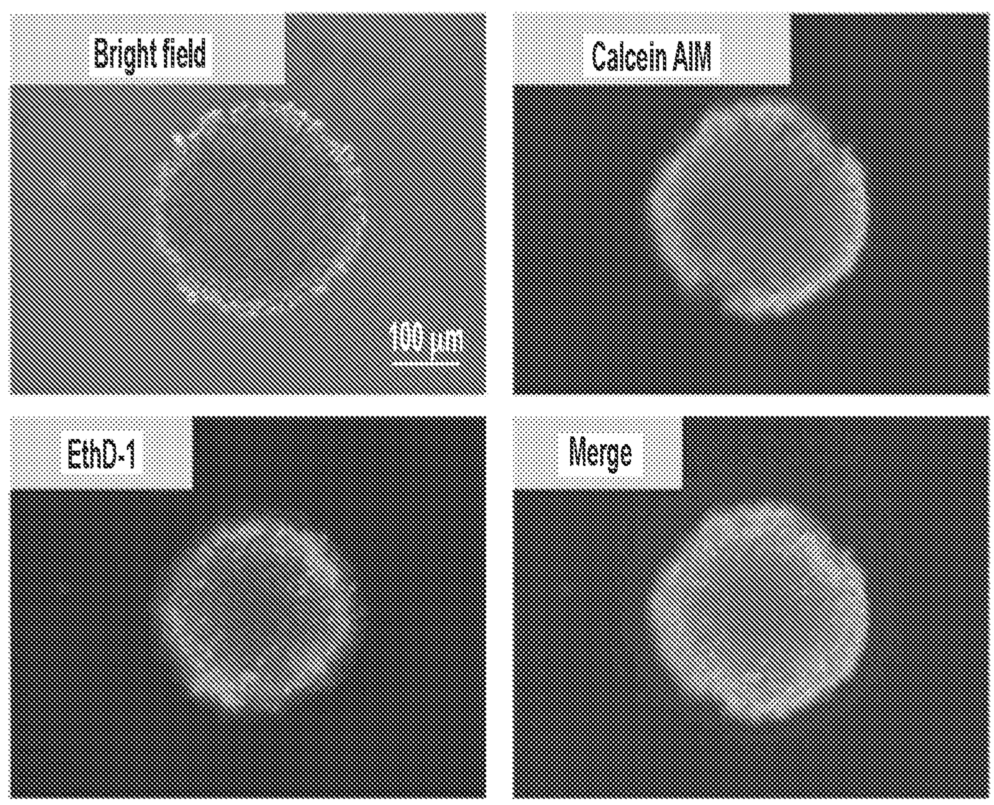
FIG. 1 shows fluorescent images demonstrating cell death in the core of a spheroid.

Spheroid viability was evaluated using a hepatoma cell line. HepG2 cells were seeded at 120K cells/mL for bulk spheroid culture in microcavity insert prototypes (with 733 microwells each) designed for a 6-well microplate. FIG. 1 shows a bright field image of a day 9 HepG2 spheroid. A fluorescent image of the day 9 HepG2 spheroid stained with Calcein AM is shown where the green color designates the Calcein AM and live cells—the green color is shown as a light gray color against a black image background. A fluorescent image of the day 9 HepG2 spheroid stained with EthD-1 is shown, where the red color designates the EthD and dead cells—the red color is shown as a medium gray color against a black image background. A merged fluorescent image of the dead cells (depicted by the red EthD staining/medium gray color) and live cells (depicted by the green Calcein AM staining/light gray color) is also shown for the day 9 HepG2 spheroid, which shows significant cell death with a ring of medium gray inside an outer ring of light gray against the black image background. Thus, the spheroid viability evaluation of Day 9 HepG2 spheroids shown in FIG. 1 demonstrates cell death in the core of spheroid.

Conventional substrates are commercially available to grow cells as 3D spheroids generally have microstructured pit-like geometries with surface coatings that are non-adherent to cells. The cells settle to the bottoms of these pits and attach to each other, then grow as cellular aggregates (i.e. spheroids). However, if the micropit is too shallow, the spheroids can easily be dislodged from the pit and lost during media exchanges. In contrast, if the micropit is too deep, it can be difficult to avoid trapping air within the micropit volume during initial addition of cell culture media to the vessel containing the micropits.

The present disclosure describes cell culture devices that introduce plastic fibers, hydrogel posts, or a combination thereof into 3D cell cultures during cell culture. The fibers or posts may be porous or gas permeable to allow for nutrient supply to the core of the spheroid, as well as to allow for waste exchange in and out of the inner mass of the 3D cell culture. Due to the features of the plastic fibers or hydrogel posts, the waste exchange occurs through a passive diffusion mode of action.

Devices according to embodiments described herein prevent the loss of spheroids during cell culture operations due to features that immobilize the 3D cell mass within wells or microcavities. In embodiments, devices described herein support tissue-like 3D culture, due to use of an artificial vascular scaffold that allows even distribution of nutrients, metabolic waste products, and oxygen within the 3D cell cultures. Moreover, embodiments of devices described herein help to avoid the formation of necrotic cores within the 3D cell cultures and increase the size of artificial tissue generated in 3D format.

Figure 2:
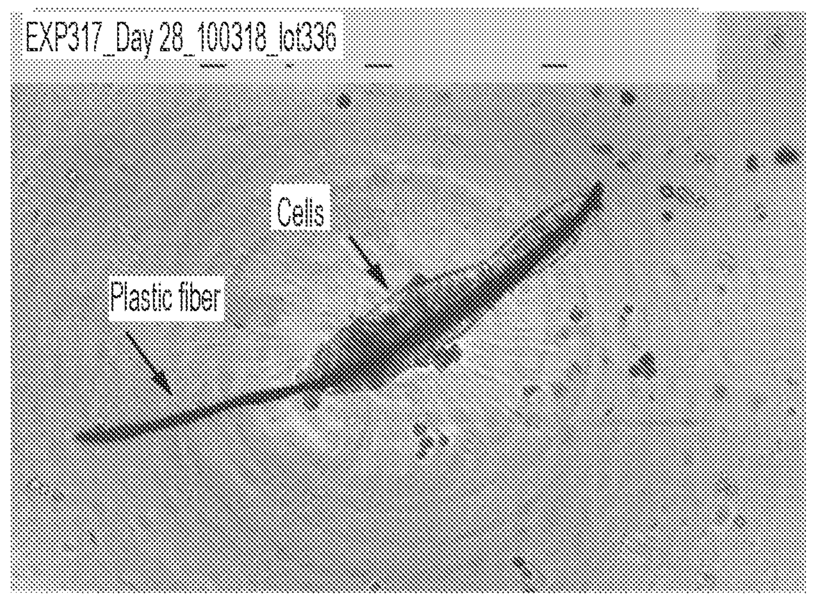
FIG. 2 shows images of cells cultured in the presence of a scaffold comprising a fiber according to one or more embodiments shown or described herein.
Figure 3:
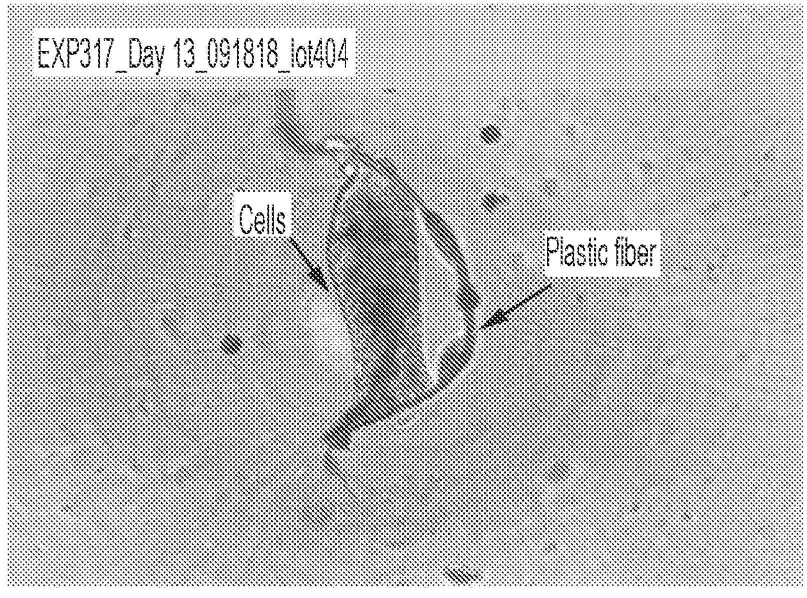
FIG. 3 shows images of cells cultured in the presence of a scaffold comprising a fiber according to one or more embodiments shown or described herein.

FIG. 2 and FIG. 3 show images of cells cultured in wells from a culture device according to an embodiment of the present disclosure. Two different donor lots of primary human hepatocytes (PHH) were used to set up liver spheroid culture. The images show liver cells within wells coated with an ultra-low attachment (ULA) surface coating in a Corning 96-well spheroid plate (Corning Incorporated, Corning, NY). The image in FIG. 2 was taken at day 28 for PHH donor lot 336, and the image in FIG. 3 was taken at day 13 for PHH donor lot 404. As shown in FIG. 2, the culture device comprises a plastic fiber in a substantially straight shape within the well, and the cells attach to the plastic fiber in a 3D configuration that is elongated along the length of the plastic fiber. As shown in FIG. 3, the culture device comprises a plastic fiber in a curved shape within the well, and the cells attach to the plastic fiber in a 3D configuration that spans from a first end of the fiber to the opposite end. The plastic fibers in FIG. 2 and FIG. 3 are disposed within the well and floating within the culture media. However, in some embodiments, plastic fibers may be anchored in the well.

In aspects described herein, a plurality of scaffolds may be disposed in a cell culture device. The cell culture device may comprise a plurality of wells, each well comprising a top aperture, a bottom, and a sidewall disposed between the top and the bottom, wherein each well is configured with an interior surface comprising a cell non-adherent surface. In an embodiment, each well in the plurality of wells of the culture device may comprise a plurality of scaffolds. In an embodiment, each well in the plurality of wells of the culture device may comprise at least one scaffold. In an embodiment, at least some of the wells in the plurality of wells of the culture device comprise scaffold(s).

In an embodiment, scaffolds described herein, such as a plastic fiber or artificial vascular scaffold, may be anchored within a well or microcavity. The scaffolds may be anchored by any suitable means that positions the scaffold securely within the well or microcavity. In nonlimiting examples, the scaffold may be secured by adhesive or molded or overmolded into the well or microcavity.

In some embodiments, the scaffold is anchored at essentially the same position within each well or microcavity within the multi-well plate, which facilitates efficient imaging of 3D cell cultures. For example, the scaffolds may be anchored to a central, bottom portion of each well or microcavity. In an embodiment, each fiber in the plurality of fibers of a fiber scaffold is anchored to the bottom, or to a portion of the bottom, of each well. An end of each fiber may be anchored to the bottom. Anchored ends of individual fibers may be distanced from adjacent anchored fibers. For example, anchored ends of individual fibers may be distanced about 100 μm to about 200 μm apart from one another in each well. In some embodiments, at least one end of a plastic fiber may be anchored in a well or microcavity and the plastic fiber may have a vertical or substantially vertical orientation within the well or microcavity. In some embodiments, opposite ends of a plastic fiber are anchored in a well or microcavity and the plastic fiber may have a horizontal or substantially horizontal orientation of the plastic fiber in the well or microcavity.

In an aspect, a cell culture device is provided that comprises a 3D cell culture diffusion structure in wells of a multi-well plate. In embodiments, the diffusion structure comprises a scaffold. The scaffold may comprise a fiber, such as the nonlimiting example of a tethering plastic fiber. In embodiments, a scaffold may be disposed in each well of a well plate. In embodiments, a scaffold may be disposed in select wells of a well plate. The well plate may comprise a plurality of wells, such as in a multi-well plate. In embodiments, an interior surface of each well is a cell non-adherent surface, such as the nonlimiting example of a surface treated or coated with an ultra-low attachment (ULA) coating. The scaffold comprises a cell-adherent surface and provides an anchoring point to a 3D cell culture, which allows for more complete medium change during the cell culture process. By anchoring the 3D cell culture, displacement or loss of the 3D cell culture is prevented during the cell culture operation or assay process, such as during medium exchange or compound dosing.

Figure 4A:
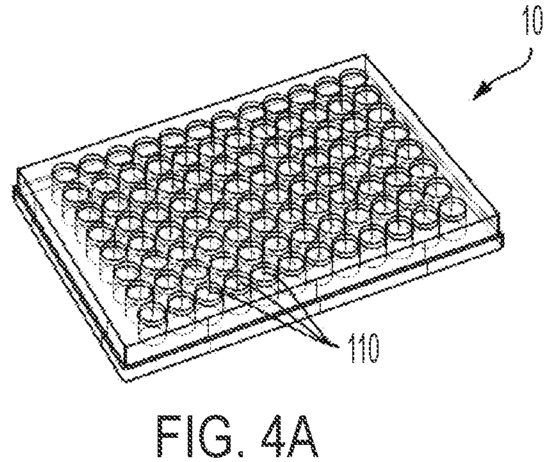
FIG. 4A, FIG. 4B, and FIG. 4C show an embodiment of a multi-well microplate, in accordance with one or more embodiments of the present disclosure.
Figure 4B:
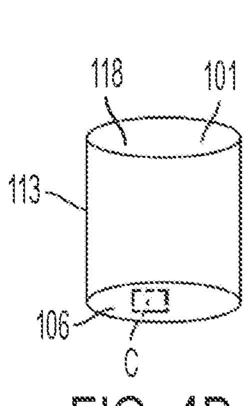
Figure 4C:
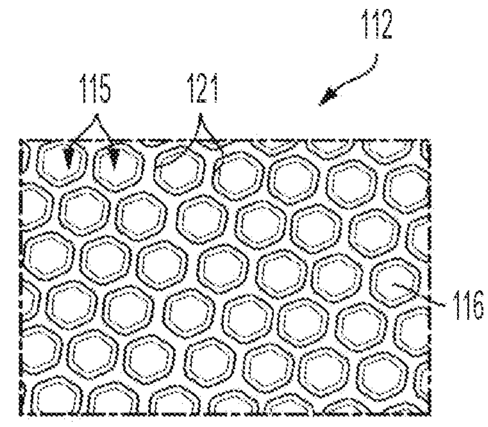

Referring now to FIG. 4A, FIG. 4B, and FIG. 4C, an embodiment of a cell culture device that is a microcavity plate is shown. The 96 well microcavity plate has an array of microcavities on the bottom surface of each well, with each microcavity structured to constrain the cultured cells to grow in a 3D conformation, to provide multiple 3D cell cultures in each of the 96 wells. FIG. 4A illustrates a multi-well plate 10 having an array of wells 110. FIG. 4B illustrates a single well 101 of the multi-well plate 10 of FIG. 4A. The single well 101 has a top aperture 118, a liquid impermeable bottom surface 106, and a sidewall 113. FIG. 4C is an exploded view of the area of the bottom surface 106 of the well 101 shown in the box C in FIG. 4B illustrating an array of microcavities 112 in the bottom surface of the single well shown in FIG. 4B. Each microcavity 115 in the array of microcavities 112 has a sidewall 121 and a liquid impermeable bottom surface 116. The microcavity spheroid plate shown in FIG. 4A, FIG. 4B and FIG. 4C, which provides an array of microcavities 112 in the bottom of each individual well 101, can be used to grow an individual 3D cell culture in each of the microcavities of each individual well of the multi-well plate. By using this type of vessel, a user can grow a large number of 3D cell cultures in each well of a multi-well plate and thereby provide a large number of 3D cell cultures that maintain prolonged viability and functionality and that can be treated under the same culture and experimental conditions for use in an assay as provided herein. Further, this type of vessel provides a physical barrier between individual 3D cell cultures to prevent any 3D cell culture fusion during culture or testing.

Figure 5A:
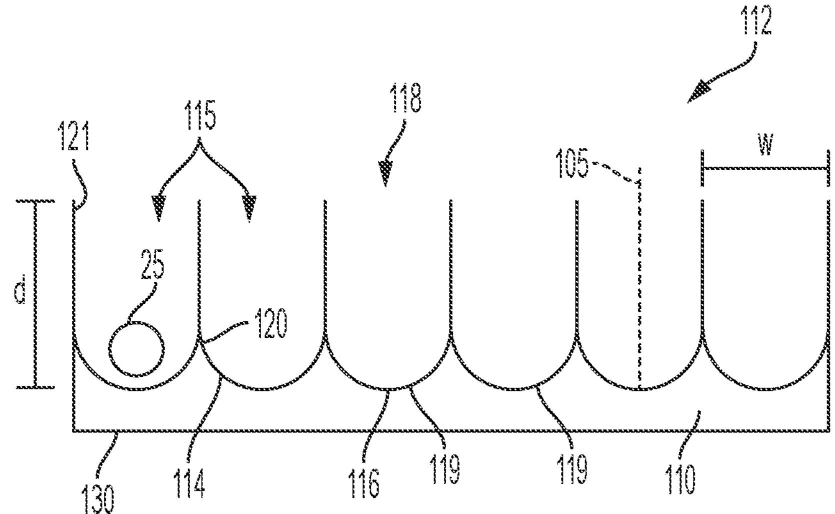
FIG. 5A and FIG. 5B show embodiments of arrays of microcavities, in accordance with one or more embodiments of the present disclosure.
Figure 5B:
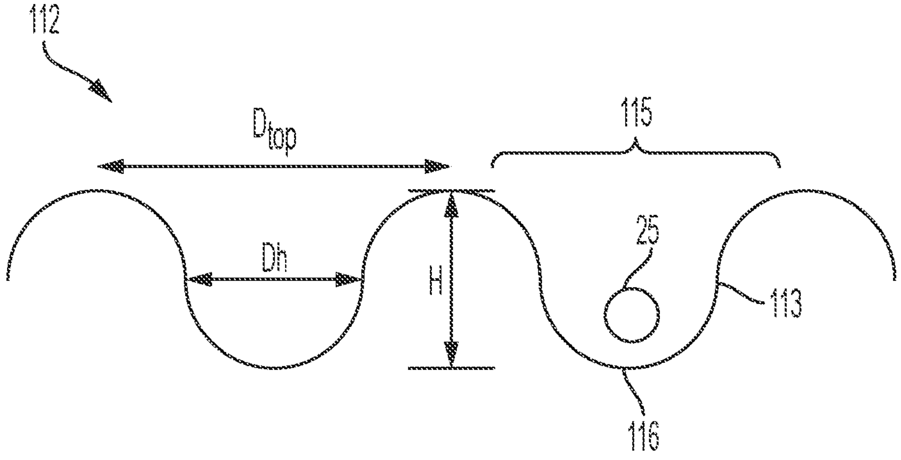

Referring now to FIG. 5A, an exemplary illustration of an array of microcavities 112 is shown. FIG. 5A illustrates microcavities 115, each having top aperture 118, a bottom surface 119, a depth d, and a width w defined by sidewalls 121. As shown in FIG. 5A and FIG. 5B, the array of microcavities have a liquid impermeable, concave arcuate bottom surface 116. In embodiments, the bottom surfaces of the microcavities can be round or conical, angled, flat bottomed, or any shape suitable for forming 3D cell cultures. In some embodiments, a rounded bottom is preferred. The round bottom 119 can have a transition zone 114 as the perpendicular sidewalls transition into a round bottom 119. This can be a smooth or angled transition zone. In embodiments, the "microcavity" can be, for example, a microwell 115 that defines an upper aperture 118 and a nadir 116, a center of the upper aperture, and a center axis 105 between the nadir and the center of the upper aperture. In embodiments, the well is rotationally symmetrical about the axis (i.e. the sidewall is cylindrical). In some embodiments, the upper aperture defines a distance across the upper aperture (width w) of from between 250 μm to 1 mm, or any range within those measurements. In some embodiments the distance from the upper aperture to the nadir (the depth "d") is between 200 μm and 900 μm, or between 400 and 600 μm. The array of microcavities may have different geometries, for example, parabolic, hyperbolic, chevron, and cross-section geometries, or combinations thereof. In embodiments, the microcavities may have a protective layer 130 below them to protect them from direct contact with a surface such as a lab bench or a table. In some embodiments, there may be an air space 110 provided between the bottom of the wells 119 and the protective layer. In embodiments, the air space 110 may be in communication with the external environment or may be closed. 3D cell cultures 25 are shown at the bottom of some individual microcavities 115.

Referring now to FIG. 5B, a further exemplary illustration of an array of microcavities 112 is shown. FIG. 5B illustrates that the array of microcavities 112 may have a sinusoidal or parabolic shape. This shape creates a rounded top edge or microcavity edge which, in embodiments, reduces the entrapment of air at a sharp corner or 90-degree angle at the top of a microcavity. As shown in FIG. 5B, in aspects the microcavity 115 has a top opening having a top diameter $D_{top}$, a height from the bottom of the microcavity 116 to the top of the microcavity H, a diameter of the microcavity at a height half-way between the top of the microcavity and the bottom 116 of the microcavity $D_H$, and a sidewall 113. In such embodiments, the bottom of the well is rounded (e.g., hemispherically round), the side walls increase in diameter from the bottom of the well to the top and the boundary between wells is rounded. As such, the top of the wells does not terminate at a right angle. In some embodiments, a well has a diameter D at the half-way point (also termed $D_H$) between the bottom and top, a diameter $D_{top}$ at the top of the well and a height H from bottom to top of the well. In these embodiments, $D_{top}$ is greater than D.

Figure 6A:
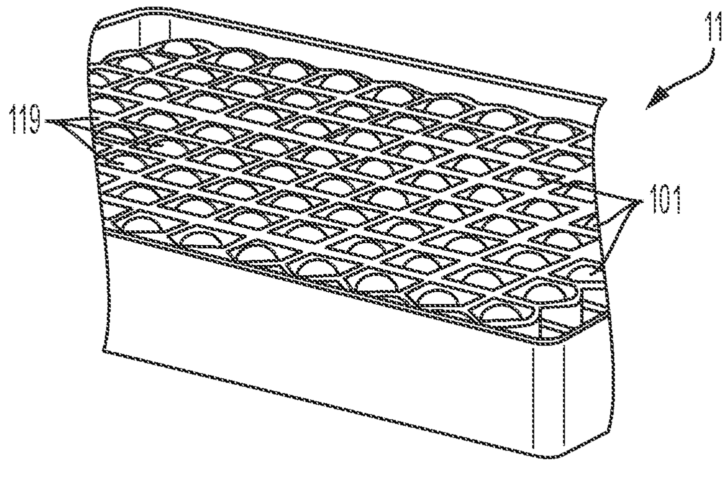
FIG. 6A and FIG. 6B show an embodiment of a 3D cell culture microplate, in accordance with one or more embodiments of the present disclosure.
Figure 6B:
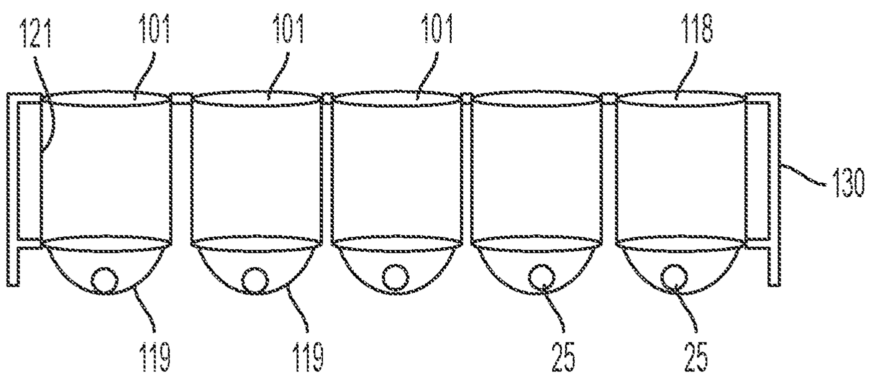

Referring now to FIG. 6A and FIG. 6B, an embodiment of a cell culture device including a well structured to constrain the cells to grow in a 3D conformation, e.g., a 3D cell culture plate, is shown. FIG. 6A shows an embodiment of a 3D cell culture plate 11, in this case a 96 well plate, with rounded bottoms 119 configured to contain a single 3D cell culture in each of the 96 wells. While usually these plates are used with the top aperture 118 of the wells 101 facing up, in FIG. 6A the plate is illustrated upside-down to show the structure of the bottoms of the wells 101. FIG. 6B is an illustration of an embodiment of a 3D cell culture microplate having a frame 130, multiple wells 101, each having a top aperture 118, a side wall 121, and a liquid impermeable, concave arcuate bottom surface 119. 3D cell cultures 25 are shown at the bottom of each individual well 101. In embodiments the frame 130 may hold the bottom of the wells above a surface such as a lab bench or a table. In some embodiments, there may be an air space provided between the bottom of the wells 119 and the surface underneath the plate. In embodiments, the air space may be in communication with the external environment or may be closed.

In embodiments, the at least one concave arcuate bottom surface of the well can have, for example, a plurality of adjacent concave arcuate bottom surfaces within the same well. Or, as shown in FIG. 4A-C, a multi-well plate may have wells with a flat bottom surface, the flat bottom surface having an array of adjacent concave arcuate bottom surfaces or microcavities within the same well. In embodiments, the cell culture device can be, for example, a single well or multi-well plate configuration having numerous "3D cell culture wells", such as a plurality of dimples or pits in the bottom or base of each well, e.g., a microcavity 3D cell culture plate. In some embodiments, the plurality of 3D cell culture wells is configured to accommodate, for example, a single or one 3D cell culture per 3D cell culture well.

In embodiments, the bottom surface of a microcavity having the at least one concave arcuate bottom surface or "cup" can be, for example, a hemi-spherical surface, a conical surface having a rounded bottom, and like surface geometries, or a combination thereof. The microcavity bottom ultimately terminates, ends, or bottoms-out in a 3D cell culture-friendly rounded or curved surface, such as a dimple, a pit, and like concave frusto-conicial relief surfaces, or combinations thereof. In embodiments, the at least one concave surface of each microcavity in the chamber includes a hemi-spherical surface, a conical surface having a taper of 30 to about 60 degrees from the side walls to the bottom surface, or a combination thereof. In some embodiments, the at least one concave arcuate bottom surface can be, for example, a portion of a hemisphere, such as a horizontal section or slice of a hemisphere, having a diameter of, for example, from about 250 to about 5,000 microns (i.e., 0.010 to 0.200 inch), including intermediate values and ranges, depending on, for example, the well geometry selected, the number of concave arcuate surfaces within each well, the number of wells in a plate, and like considerations. Other concave arcuate surface can have, for example, parabolic, hyperbolic, chevron, and like cross-section geometries, or combinations thereof.

In embodiments, the cell culture device comprising a well, e.g., a 3D cell culture plate or a microcavity 3D cell culture plate, can further comprise a cell non-adherent surface. Each well of the cell culture plate may comprise an interior surface configured with a cell non-adherent surface. For example, the cell non-adherent surface may comprise a low-adhesion, ultra-low adhesion, or no-adhesion coating on a portion of the well, such as on the at least one concave surface and/or one or more sidewalls. Examples of a cell non-adherent material include perfluorinated polymers, olefins, or like polymers, or mixtures thereof. Other examples include agarose, non-ionic hydrogels such as polyacrylamides, or polyethers such as polyethyleneoxide or polyols such as polyvinylalcohol, or like materials, or mixtures thereof.

In embodiments, the side wall surface (i.e., a surround) can be, for example, a vertical cylinder or shaft, a portion of a vertical conic of decreasing diameter from the well top to the well bottom, a vertical square shaft or vertical oval shaft having a conical transition, i.e., a square or oval at the top of the well, transitioning to a conic, and ending with a bottom having at least one concave arcuate surface, i.e., rounded or curved, or a combination thereof. Other illustrative geometric examples include holey cylinders, holey conic cylinders, first cylinders then conics, and other like geometries, or combinations thereof.

One or more of, for example, a cell non-adherent surface or low-attachment substrate, the well curvature in the body and base portions of the cell culture article chambers, and gravity, can induce tumor cells to self-assemble into 3D cell cultures. Tumor cells maintain differentiated cell function indicative of a more in vivo-like, response relative to cells grown in a monolayer. In embodiments, the 3D cell culture may have a spheroid-like shape with a diameter of, as non-limiting examples, from about 100 to about 500 microns, from about 150 to about 400 microns, from about 150 to about 300 microns, and from about 200 to about 250 microns, including intermediate values and ranges, depending on, for example, the types of cells in the 3D cell culture.

In embodiments, the cell culture device, including the well and/or each microcavity within the chamber, can further include opaque sidewalls and/or a gas permeable and liquid impermeable bottom comprising at least one concave surface. Opaque sidewalls prevent crosstalk between wells or microwells when fluorescent imaging is employed. In some embodiments, at least a portion of the bottom comprising at least one concave surface is transparent. Cell culture devices (e.g., a microcavity spheroid plate, a microcavity insert, a microcavity insert plate, etc.) having such features can provide several advantages for the instantly-disclosed methods, including removing the need for transferring the 3D cell cultures from one multiwall plate (in which 3D cell cultures are formed and can be visualized) to another plate for conducting assays, therefore saving time and avoiding any unnecessary disruption of the 3D cell cultures. Further, a gas-permeable bottom (e.g., well-bottoms made from a polymer having gas permeable properties at a particular given thickness) can allow the 3D cell cultures to receive increased oxygenation. An exemplary gas-permeable bottom can be formed from perfluorinated polymers or polymers such as poly 4-methylpentane at certain thicknesses.

Representative thickness and ranges of gas permeable polymers can be, for example, from about 0.001 inch to about 0.025 inch, from 0.0015 inch to about 0.03 inch, including intermediate values and ranges (where 1 inch=25,400 microns; 0.000039 inches=1 micron). Additionally, or alternatively, other materials having high gas permeability, such as polydimethylsiloxane polymers, can provide sufficient gas diffusion at a thickness, for example, of up to about 1 inch.

Figure 7:
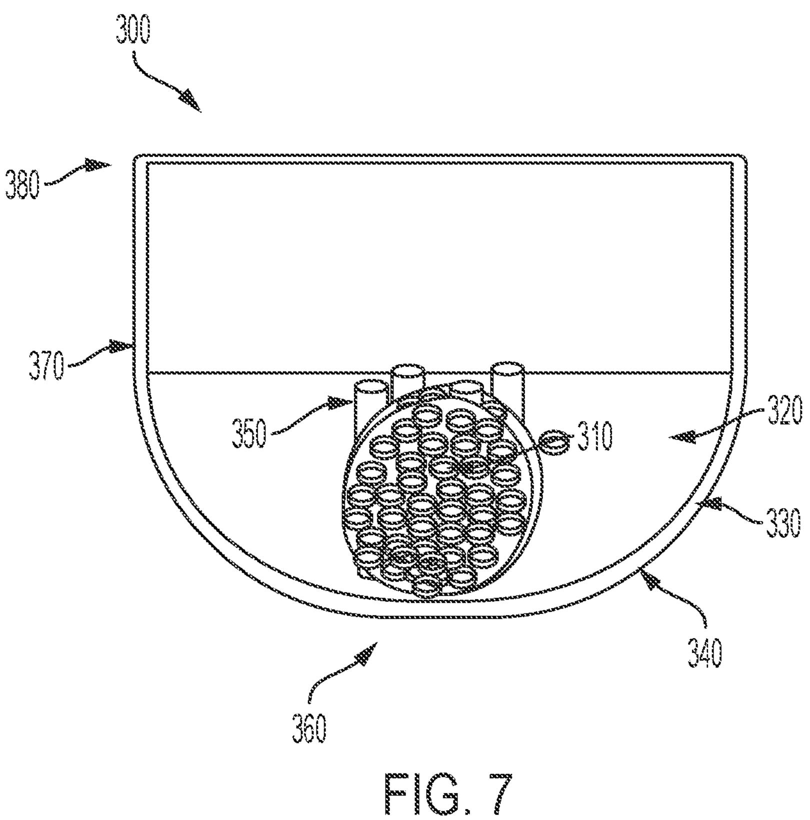
FIG. 7 shows a cross-sectional side view of a well with a tethering fiber according to one or more embodiments shown or described herein.

FIG. 7 shows a cross-sectional side view of a well or microcavity 300 in a cell culture device comprising a diffusion structure or scaffold. As shown in FIG. 7, the scaffold is a tethering scaffold or tethering plastic fiber according to an embodiment. The tethering scaffold or plastic fiber has an adherent surface to allow cell attachment and provides mechanical support and immobilization for 3D cell cultures. A sidewall 370 is disposed between the top 380 of the well or microcavity and the bottom 360 of the well or microcavity. The bottom 360 of the well or microcavity may comprise a hemispherical shape. The interior or inner surface 340 of the well or microcavity may comprise a cell non-adherent surface, such as a ULA surface 330. A tethering plastic fiber 350 may be disposed within the well or microcavity and is an anchoring point for a 3D cell culture 310. In some embodiments, a plurality of tethering plastic fibers may be disposed in the well or microcavity.

In some embodiments, the scaffold or scaffolds, such as a fiber or fibers, are attached to a bottom of a microcavity, which allows the microcavity to be shallower while still retaining the 3D cell culture during media exchanges. This occurs because the 3D cell culture grows around and, in some embodiments, attaches to these fibers or posts that form the scaffold. In this way, air entrapment becomes insignificant during initial media introduction to the vessel.

The tethering scaffold may be anchored to the well or microcavity by any suitable means. As a nonlimiting example, a scaffold may comprise a plastic fiber, which may be anchored by molding the plastic fiber into the well or microcavity. Culture media 320 is disposed in the well or microcavity 300 in an amount that covers the 3D cell culture 310 and plastic fiber 350. The well or microcavity 300 has a ULA surface 330 on the inner surface 340, and the ULA surface prevents the cells from attaching to the inner surface of the well or microcavity.

A scaffold as described herein may comprise a fiber or a plurality of fibers. The scaffold may be formed of any suitable material that is capable of tethering cells to form a 3D cell culture. In an embodiment, each well of a cell culture device may have fiber scaffolds formed of different materials. In an embodiment, each well of a cell culture device may have fiber scaffolds formed of a same material. For example, a fiber may be a plastic fiber or polymer fiber formed from polystyrene, polypropylene, polyacrylamide, polyvinylalcohol, polyvinylpyrrolidone, poly(2-hydroxyethyl methacrylate), polygalacturonic acid (PGA or pectin), and/or combinations thereof.

In embodiments where PGA is used, attached 3D cell cultures may be released or harvested from the scaffold. For example, an enzyme and/or chelating agent, such as pectinase, may be used to digest the scaffold. Methods using scaffolds as described herein may optionally comprise a digesting step wherein the scaffold is digested by adding an enzyme and/or chelating agent after cell culture or at a prescribed time during cell culture. In some embodiments, other hydrogels may be used that allow gentle digestion of the scaffold to release the 3D cell cultures.

In some embodiments, the fiber may be free-floating within the well. In some embodiments, the fiber may be anchored to a part of the well. For example, the fiber may be anchored on one end to a bottom of the well. In some embodiments, the fiber is shaped or formed, such as in a substantially straight shape, shaped in the form of an arc or curved shape, or shaped in the form of a circle.

The scaffold may be of any size that allows the scaffold to be disposed within the well or microcavity and allow sufficient space for cell culture. Scaffolds disposed in the cell culture device may vary in dimension. In some embodiments, scaffolds have an average length of about 100 μm to about 3000 μm. In some embodiments, scaffolds have an average length of about 100 μm to about 1000 μm. In some embodiments, scaffolds have an average length of about 100 μm to about 500 μm. In some embodiments, scaffolds have an average width of about 10 μm to about 100 μm. In some embodiments, scaffolds have an average width of about 10 μm to about 50 μm. In some embodiments, scaffolds have an average width of about 10 μm to about 20 μm.

Any suitable multi-well plate for cell culture may be used in cell culture devices according to embodiments described herein. In some embodiments, the cell culture device is a multi-well plate, such as a 6-well plate, a 96-well plate, 384-well plate, or a 1536-well plate. The well plate includes a plurality of wells, with the amount of wells arranged within the well plate varying depending on the size and application of the well plate. In some embodiments, the cell culture device further comprises a microcavity insert. For example, the well plate may be a ninety-six (96) well, ultra-low attachment surface, sterile spheroid microplate (available from Corning Incorporated; Corning, NY; Catalog no. 4515, 4520). For example, scaffolds according to embodiments described herein may comprise any suitable multi-well plate, such as Corning 96-well or 384-well spheroid plates (available from Corning Incorporated; Corning, NY) and Elplasia microcavity well plates (available from Corning Incorporated; Corning, NY). The well plate may be manufactured from glass, plastic, or similar materials. The well plate may optionally have a lid, the lid configured to be arranged over the top of the well plate in order to prevent foreign substances from entering the plurality of wells. The lid may fit tightly on the well plate, or may be secured to the well plate through alternative means, such as tape, elastic bands or the like.

The well plate includes a cell culture arranged within each of the wells. The cell culture is arranged and developed within each of the plurality of wells of the well plate. Culture media is also arranged within each of the plurality of wells of the well plate, where the culture media encapsulates the cell culture and is utilized to remove any air pockets within the wells. The cell culture may have formed a 3D cell culture within the well plate after being developed for a period of time (i.e., ~6 days). In some instances, the cell culture may be developed by placing the well plate within an incubator (not shown). In some embodiments, prior to placing the cell culture within the wells, the well plate may be sterilized.

Methods according to embodiments of the present disclosure may comprise culturing cells on a cell culture device. In cell culture devices comprising a scaffold within each well or microcavity, culturing cells into a 3D cell culture may include seeding cells on the scaffold disposed in the well. Seeding cells on the scaffold may include contacting the scaffold or wells with a solution containing the cells. During seeding cells on the scaffold, the cells adhere to the surface of the scaffold. Culturing cells on scaffolds may further include contacting the scaffolds with cell culture medium. Generally, contacting the scaffolds with cell culture medium includes placing cells to be cultured on the scaffolds in an environment with medium in which the cells are to be cultured. Contacting the scaffolds with cell culture medium may include pipetting cell culture medium onto the scaffolds, or submerging the scaffolds in cell culture medium, or passing cell culture media over the scaffolds in a continuous manner.

In an aspect, cell culture devices according to embodiments described herein comprise an artificial vascular scaffold to support a more tissue-like 3D cell culture. The artificial vascular scaffold may comprise a plurality of fibers that are branched, touching, and/or in contact with one another. The cell culture device allows for a 3D tissue-like culture because the artificial vascular scaffold allows the diffusion of oxygen and nutrients into the inner mass of the 3D cellular structure while allowing metabolic waste products to more easily diffuse outward (i.e. towards the inner sidewall of the well). The cell culture device comprises a multi-well cell culture plate having a plurality of wells and/or a plurality of microcavities.

Figure 8:
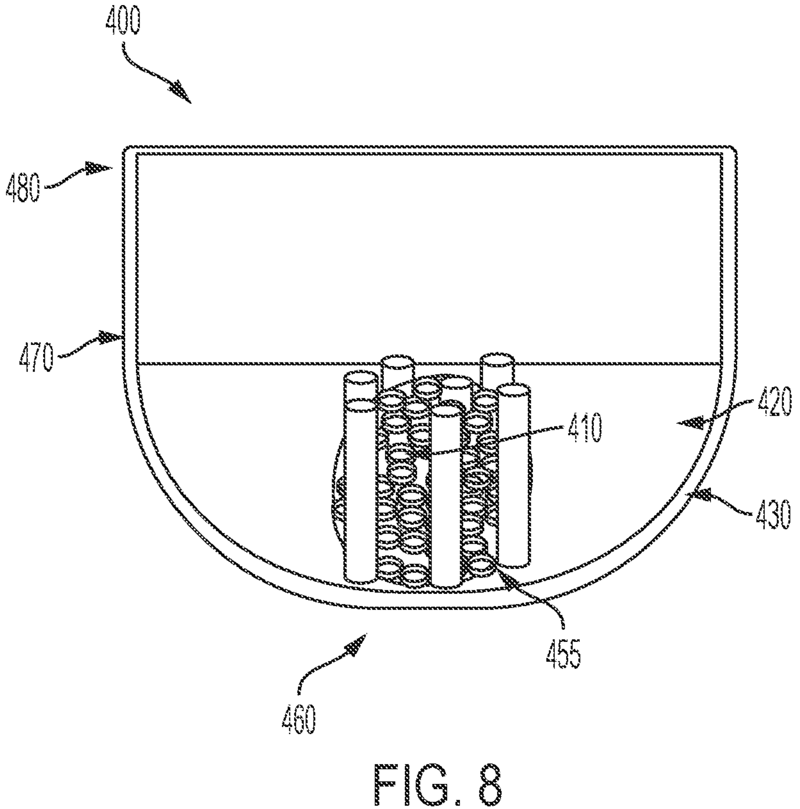
FIG. 8 shows a cross-sectional side view of a well with an artificial vascular scaffold according to one or more embodiments shown or described herein.
Figure 9:
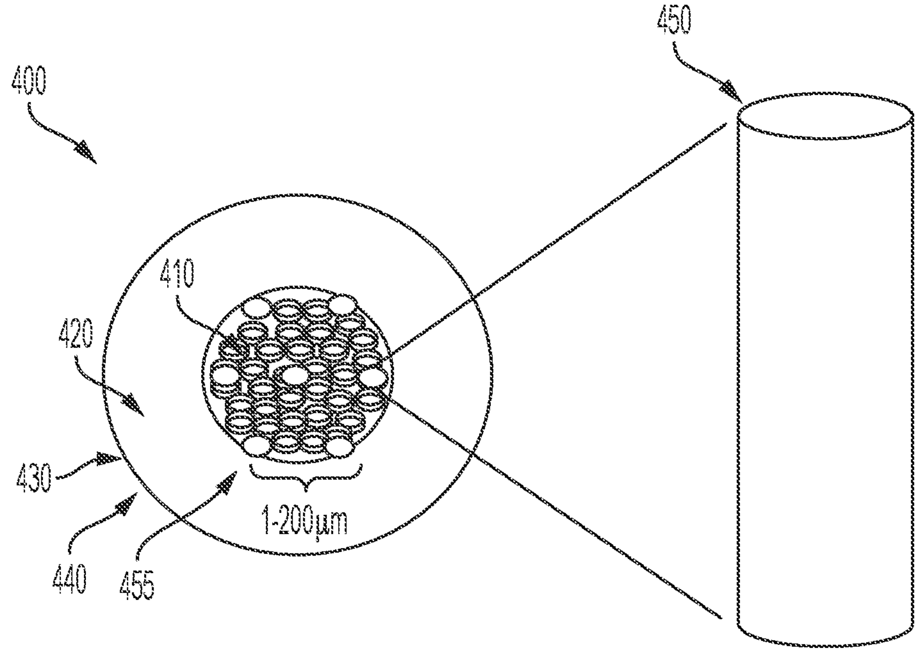
FIG. 9 shows a top view of the well of FIG. 8, with an inset of a vascular scaffold according to one or more embodiments shown or described herein.

FIG. 8 shows a cross-sectional side view of a well or microcavity with an artificial vascular scaffold according to one or more embodiments shown or described herein. FIG. 9 shows a top view of the well or microcavity of FIG. 8, with an inset of a vascular scaffold according to one or more embodiments shown or described herein. The well or microcavity 400 comprises a top 480, a bottom 460, and a sidewall 470 disposed between the top 480 and bottom 460. The well or microcavity 400 comprises an inner or interior surface 440 having a surface 430 that is non-adherent to cells. In some embodiments, the cell non-adherent surface 430 is an ultra-low attachment (ULA) surface. Cells are seeded into the wells/microcavities of the cell culture device and cell culture media 420 is disposed within the wells/microcavities.

An artificial vascular scaffold 455 having a cell adherent surface is disposed within the well/microcavity and may be anchored to the well/microcavity bottom 460. The artificial vascular scaffold may be anchored by any suitable means, such as by an adhesive or formed by molding or overmolding. In some embodiments, the artificial vascular scaffold comprises a plurality of fibers 450 that have a cell-adherent surface. In some embodiments, a fiber 450 of the artificial vascular scaffold 455 is shaped like a post or column and is anchored at one end to the bottom 460 of the well/microcavity 400. In some embodiments, the artificial vascular scaffold comprises a plurality of fibers, with fibers arranged at a distance of about 100 μm to about 200 μm from each other.

The artificial vascular scaffold 455 may be formed from any suitable material that allows for passive diffusion of medium carrying nutrients and oxygen. For example, the artificial vascular scaffold may comprise a hydrogel material or a hollow fiber. The hollow fiber or hydrogel material allows passive diffusion of medium carrying nutrients and oxygen from the cell culture media 420 to the interior of the 3D cell culture 410. The artificial vascular scaffold may be made of non-ionic polymers. Non-limiting examples of non-ionic polymers include polystyrene, polypropylene, polyvinylalcohol, polyvinylpyrrolidone (PVP), polyacrylamide, poly(2-hydroxyethyl methacrylate) (pHEMA), polygalacturonic acid (PGA or pectin), and/or combinations thereof. In embodiments where PGA is used, attached 3D cell cultures may be released or harvested from the scaffold. For example, an enzyme and/or chelating agent, such as pectinase, may be used to digest the scaffold. A hydrogel material may be applied to the artificial scaffold, such as by surface coating, molding, or printing the hydrogel material on the scaffold. The hydrogel can consist of any materials known in the art and can be produced to be either adherent or non-adherent to cells. For example, in some embodiments, the hydrogel fibers are formed of ECM proteins, decellularized tissue ECM scaffolds, ECM peptide sequences, crosslinked polymers, or a combination thereof. Non-limiting examples of adherent hydrogels comprise ECM proteins and decellularized tissue ECM scaffolds. ECM examples include polysaccharide glycosaminoglycans (GAGs) and proteins such as collagens, laminins, and fibronectin. Non-limiting examples of non-adherent hydrogels comprise crosslinked polymers such as polyethylene oxide, polyvinyl alcohol, polyvinyl pyrrolidone, polyacrylamide, and polygalacturonic acid (PGA), among others. In some embodiments, other hydrogels may be used that allow gentle digestion of the scaffold to release the 3D cell cultures. In some embodiments, the hydrogel is formed from a non-attachment hydrogel and comprises a surface functionalized with attachment groups. Non-limiting examples of attachment groups include ECM proteins and attachment peptide sequences, such as arginylglycylaspartic acid (RGD).

Cells seeded in the well/microcavity may attach to the artificial vascular scaffold or form around the artificial vascular scaffold. During cell culture, the cells continue to grow to form a 3D cell mass between fibers within the scaffold and around the artificial vascular scaffold. As the 3D cell mass grows during cell culture, the hollow fiber or hydrogel material of the artificial vascular scaffold allows passive diffusion of medium carrying nutrients and oxygen from the cell culture media 420 to the interior of the 3D cell culture 410. Because of the diffusible feature of the artificial vascular scaffold, nutrients and oxygen are more evenly supplied throughout the volume of the 3D cell culture. In addition, the diffusion provided by the artificial vascular scaffold allows for metabolic waste product concentrations to be more evenly depleted throughout the volume of the 3D cell culture. As such, the diffusion features of the artificial vascular scaffold allow for production of larger 3D cell culture volumes before necrotic core formation occurs. Moreover, the artificial vascular scaffold provides mechanical support and immobilization of a 3D cell mass within the well/microcavity. By immobilizing the 3D cell mass, imaging of the 3D cell cultures is simplified. Instead of focusing on many differing portions of wells or microcavities and searching for presence or location of 3D cell cultures, a user can instead focus the imaging equipment on the artificial vascular support which is embedded within the 3D cell mass. Moreover, the artificial vascular support may be anchored at a uniform location throughout the wells or microcavities. As a nonlimiting example, in some embodiments, the artificial vascular support is centralized within each well or microcavity and is anchored at a center, bottom portion of the well or microcavity.

Figure 10:
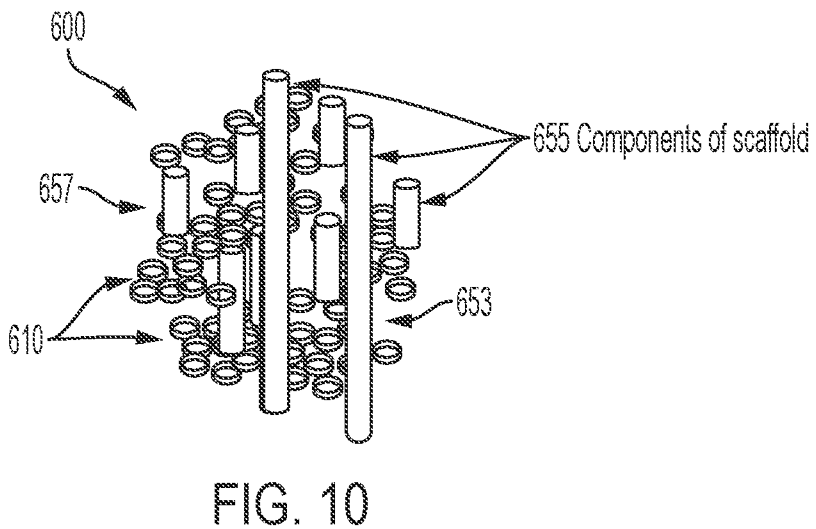
FIG. 10 shows a side perspective view of a hydrogel scaffold according to one or more embodiments shown or described herein.

In an aspect, a cell culture device comprises a hydrogel scaffold as shown in FIG. 10. FIG. 10 shows a side perspective view of a hydrogel scaffold 600 according to one or more embodiments shown or described herein. The hydrogel scaffold 600 comprises hydrogel fibers 655, 653, 657 having different lengths. For example, hydrogel fiber 653 has a longer length than hydrogel fiber 657. The hydrogel fibers of the scaffold have a cell-adherent surface, and 3D cell culture 610 forms from cells adhering to the hydrogel scaffold.

The hydrogel allows for passive diffusion of compounds into and out of the 3D cell culture, thus helping to eliminate the formation of necrotic cores due to greatly improved diffusive exchange of gases, nutrients, and metabolic wastes. In some embodiments, the fiber is formed of a hydrogel material. In some embodiments, the fiber or post is formed of a solid material, such as a polymer like polystyrene, which is then coated with a hydrogel at a thickness sufficient to allow for diffusive exchange to the core of the 3D cell culture. In an embodiment, the hydrogel fibers or posts are in the form of free hydrogel fibers that are deposited into the microcavities before cell seeding or during cell seeding. The hydrogel can comprise any materials known in the art and can be produced to be either adherent or non-adherent to cells. In some embodiments, the hydrogel fibers are formed of extracellular matrix (ECM) proteins, decellularized tissue ECM scaffolds, ECM peptide binding sequences, or crosslinked polymers. Non-limiting examples of adherent hydrogels comprise ECM proteins, decellularized tissue ECM scaffolds, and ECM peptide sequences. ECM examples include polysaccharide glycosaminoglycans (GAGs) and proteins such as collagens, laminins, and fibronectin. In some embodiments, the hydrogel fiber is formed from a non-attachment hydrogel and comprises a surface functionalized with attachment groups. Non-limiting examples of attachment groups include ECM proteins and attachment peptide sequences, such as arginylglycylaspartic acid (RGD). Non-limiting examples of non-adherent hydrogels comprise crosslinked polymers such as polyethylene oxide, polyvinyl alcohol, polyvinyl pyrrolidone, polyacrylamide, and polygalacturonic acid (PGA), among others.

Figure 11:
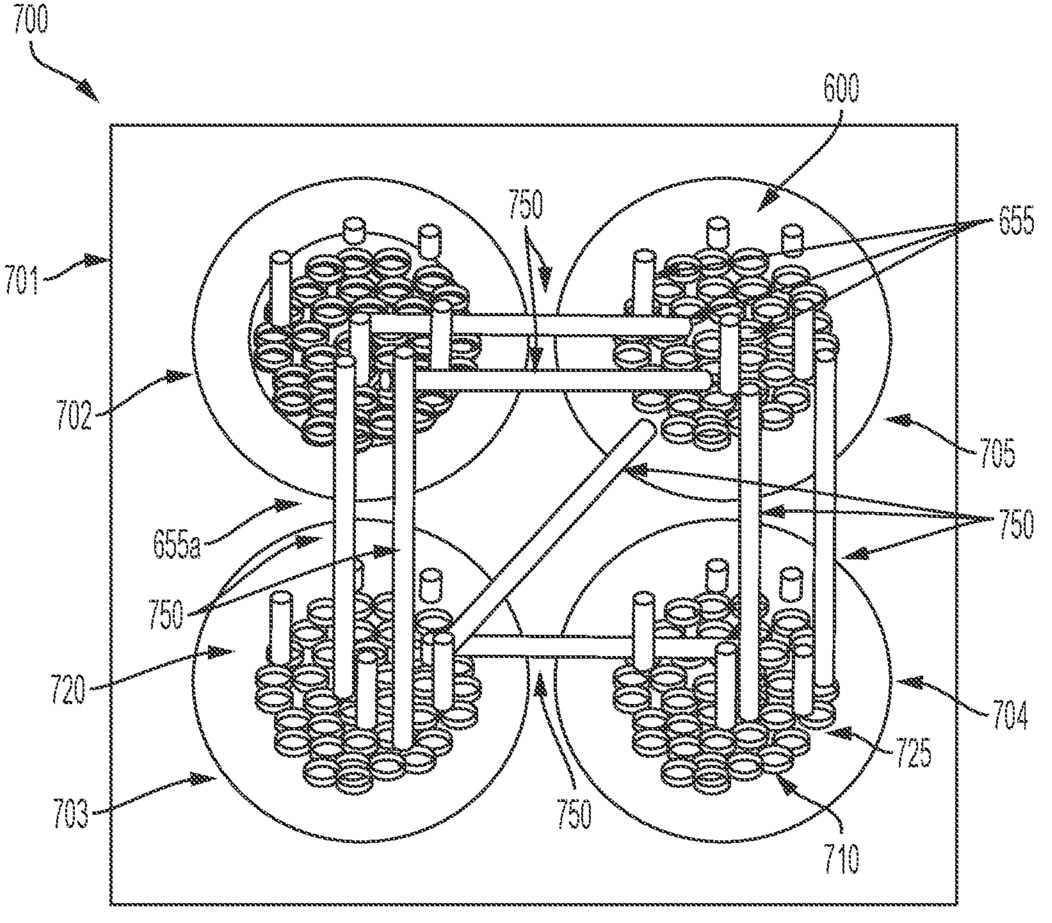
FIG. 11 shows a top view of interconnected wells having a hydrogel scaffold according to one or more embodiments shown or described herein.

In embodiments, hydrogel scaffolds allow an interconnected cell culture device to be formed that comprises hydrogel channels between 3D cell cultures within wells/microcavities of the device, as shown in FIG. 11. To form an interconnected cell culture device, pre-made hydrogel scaffold fibers may be mixed with cells during initial setting up of the culture device for 3D cell cultures. As a result, hydrogel scaffolds of different sizes will be present inside the 3D cell culture structures. For example, a mixture comprising a cell suspension and hydrogel scaffolds may be prepared and applied to a multi-well cell culture plate for bulk culture of 3D cell cultures. A non-limiting example of a multi-well cell culture plate for bulk culture of 3D cell cultures includes an Elplasia 24-well microcavity plate (available from Corning Incorporated; Corning, NY). Because of the diffusible feature of the scaffold, nutrients and oxygen are more evenly supplied throughout the volume of the 3D cell culture and conversely, metabolic waste product concentrations are also more evenly depleted throughout the volume of the 3D cell culture. This allows for production of larger 3D cell culture volumes before necrotic core formation occurs in the 3D cell culture.

FIG. 11 shows a top view of interconnected wells or microcavities 702-705 in an interconnected cell culture device 700 according to one or more embodiments shown or described herein. Embodiments of the disclosure comprise a multi-well cell culture plate 701. The cell culture plate may comprise a plurality of wells and/or a plurality of microcavities 702, 703, 704, 705, and the interior surface of the wells or microcavities may further comprise a non-adherent surface to prevent cell attachment. To create the hydrogel scaffolds 600, cells 710 are seeded along with hydrogel fibers 655 in the wells or microcavities 702-705 of the cell culture plate 701.

Due to the combination of the non-adherent surface of the wells and/or microcavities 702-705, and the cell adherent surface of the hydrogel fibers 655, and cells 710 attach to the surface of the hydrogel fibers 655 in the hydrogel scaffold 600. With nutrients supplied from the cell culture media 720 disposed in the wells or microcavities 702-705, the cells 710 continue to grow between and around the hydrogel fibers 655 within the hydrogel scaffold 600 to form a 3D cell culture 725. Moreover, because the hydrogel fibers are of different sizes and lengths, the fibers of one scaffold may also be embedded into 3D cell cultures in neighboring microcavities/wells. For example, an interconnected cell culture device is formed from diffusion paths or hydrogel channels 750 that are created when opposite ends of hydrogel fibers are located in different wells or microcavities. As an example, one end of hydrogel fiber 655*a* is located in well/microcavity 702, while the opposite end of hydrogel fiber 655*a* is located in neighboring well/microcavity 703 to create a hydrogel channel 750 between wells or microcavities 702 and 703. The hydrogel fibers and hydrogel channels act as diffusion paths that allow for passive diffusion to and from the 3D cell culture cores and allow for nutrients to be supplied inside the 3D cell cultures as well as the across the whole culture. Furthermore, the hydrogel fibers provide a physical connection with the interconnected wells or microcavities, and that physical connection prevents the loss of 3D cell cultures during operations such as medium exchange or drug testing.

Any type of cell may be cultured in embodiments of the cell culture devices including, but not limited to, immortalized cells, primary culture cells, cancer cells, stem cells (e.g., embryonic or induced pluripotent), etc. Though 3-dimensional cell culture is contemplated in embodiments described herein, the cells may be in any cultured form including disperse (e.g., freshly seeded), confluent, 2-dimensional, 3-dimensional, spheroid, etc., when introduced to cell culture devices according to embodiments of the disclosure. The cells may be mammalian cells, avian cells, piscine cells, etc. The cells may be of any tissue type including, but not limited to, kidney, fibroblast, breast, skin, brain, ovary, lung, bone, nerve, muscle, cardiac, colorectal, pancreas, immune (e.g., B cell), blood, etc. In some embodiments, the cell culture is a live cell culture. In some embodiments, the cell culture is a liver spheroid which is made from primary human hepatocytes (PHH). However, it should be understood that other types of cell cultures are contemplated and possible.

Any cell culture medium capable of supporting the growth of cells may be used. Cell culture medium may be for example, but is not limited to, sugars, salts, amino acids, serum (e.g., fetal bovine serum), antibiotics, growth factors, differentiation factors, colorant, or other desired factors. Exemplary cell culture medium includes Dulbecco's Modified Eagle Medium (DMEM), Ham's F12 Nutrient Mixture, Minimum Essential Media (MEM), RPMI Medium, Iscove's Modified Dulbecco's Media (IMDM) Mesencult-XF medium, and the like. Furthermore, cell culture medium may be removed and replaced according to any predetermined schedule. For example, at least some of the cell culture medium may be removed and replaced every hour, or every 12 hours, or every 24 hours, or every 2 days, or every 3 days, or every 4 days, or every 5 days, or the like.

As used herein, in some embodiments, the cell culture article includes from 1 to about 2,000 wells, wherein each well is physically separated from any other well. In embodiments the wells are wells of a multi-well plate. For example, a cell culture device may be a flask with a single well or chamber, having an array of microcavities on a cell culture surface or bottom surface. A cell culture device may be a multi-well plate having 1, 6, 12, 24, 96, 384 or 1536 wells. In some embodiments, each well includes from about 25 to about 1,000 microcavities.

As used herein, in some embodiments, a well is an individual cell culture environment provided in a multi-well plate format. In embodiments, a well can be a well of a 4 well plate, a 6 well plate, a 12 well plate, a 24 well plate, a 96 well plate, a 538 well plate, a 1536 well plate, or any other multi-well plate configuration. In some embodiments, a well of a multi-well plate can be structured to constrain cells of interest to grow as a single 3D cell mass in that single well. For example, a well of a 96 well plate (wells of traditional 96 well plates) are approximately 10.67 mm deep, have a top aperture of approximately 6.86 mm and a well bottom diameter of approximately 6.35 mm In embodiments, a 3D cell culture plate means a multi-well plate having an array of single 3D cell culture chambers or wells. That is, in embodiments, a multi-well plate may have multiple chambers or wells, wherein each chamber or well is configured to contain a single 3D cell culture or 3D cell mass.

As used herein, a microwell or microcavity is structured to constrain cells of interest to grow in 3D conformation and has dimensions or treatments, or a combination of dimensions and treatments, which encourage cells in culture to grow in 3D conformation rather than as two-dimensional sheets of cells. Treatments include treatment with low binding solutions, treatments to render the surface less hydrophobic, or treatments for sterilization, for example.

As used herein, in some embodiments, a well may have an array of microcavities or a plurality of microcavities. In embodiments, the microcavity or microwell can be, for example, a microwell that defines an upper aperture and a nadir, a center of the upper aperture, and a center axis between the nadir and the center of the upper aperture. In embodiments, the microcavity or microwell well is rotationally symmetrical about the axis (i.e. the sidewall is cylindrical). In some embodiments, the upper aperture defines a distance across the upper aperture of from between 250 μm to 1 mm, or any range within those measurements. In some embodiments, the distance from the upper aperture to the nadir (the depth "d") is between 200 μm and 900 μm. In some embodiments, the distance from the upper aperture to the nadir (the depth "d") is between 400 μm and 600 μm. In some embodiments, the distance from the upper aperture to the nadir (the depth "d") is at least 200 μm. In some embodiments, the distance from the upper aperture to the nadir (the depth "d") is at least 2500 μm. In some embodiments, the distance from the upper aperture to the nadir (the depth "d") is at least 400 μm. In some embodiments, the distance from the upper aperture to the nadir (the depth "d") is not more than 1 mm. In some embodiments, the distance from the upper aperture to the nadir (the depth "d") is not more than 900 μm. In some embodiments, the distance from the upper aperture to the nadir (the depth "d") is not more than 600 μm. The array of microcavities may have different geometries, for example, parabolic, hyperbolic, chevron, and cross-section geometries, or combinations thereof.

As used herein, in embodiments, a round bottom of a well or microcavity well can be, for example, a hemisphere, or a portion of a hemisphere, such as a horizontal section or slice of a hemisphere making up the bottom of the well or microcavity.

As used herein, in embodiments, a microcavity plate means a multi-well plate having an array of wells, each well having an array of microcavities. As used herein, an insert means a cell culture well that fits into a well of a plate or a microcavity plate. The insert has sidewalls and a bottom surface defining a cavity for culturing cells. As used herein, an insert plate means an insert plate containing an array of inserts structured to fit into an array of wells of a multi-well plate. As used herein, a microcavity insert plate means an insert plate in which each insert in the array of inserts has a bottom surface with an array of microcavities.

As used herein, in embodiments, the term "3D cell culture" can be, for example, a grouping of cells in culture which are not a flat, two-dimensional (2D) sheet of cells. In some embodiments, the 3D cell culture may resemble a 3D spheroid-like shape, or a shape resembling an aggregate or ball of cells in culture, which are not a flat two-dimensional sheet of cells. In embodiments, the 3D cell culture is comprised of a single cell type or multiple cell types. In embodiments where the 3D cell culture resembles a 3D spheroid-like shape, the 3D cell culture may have a diameter of, for example, from about 100 to about 500 microns, more preferably from about 150 to about 400 microns, even more preferably from about 150 to about 300 microns, and most preferably from about 200 to about 250 microns, including intermediate values and ranges, depending on, for example, the types of cells in the 3D cell culture.

In an aspect, a cell culture device comprises a multi-well cell culture plate comprising a plurality of wells, each well comprising a top aperture, a bottom, and a sidewall disposed between the top and the bottom, wherein each well is configured with an interior surface comprising a cell non-adherent surface; and a plurality of scaffolds disposed within the plurality of wells of the multi-well cell culture plate, each scaffold comprising a cell-adherent surface. The bottom may comprise a hemispherical shape. At least one scaffold may be disposed in each well. A plurality of scaffolds may be disposed in each well. At least some of the wells of the plurality of wells may have a scaffold disposed therein.

At least a portion of the scaffold may be anchored to a bottom, or portion of the bottom or each well. At least one end of the scaffold may be anchored to a bottom portion of each well.

The bottom may comprise a plurality of microcavities. A scaffold may be disposed in each microcavity of the plurality of microcavities. The scaffold may be anchored to a bottom portion of each microcavity.

The scaffold may have an average length in a range of about 100 μm to about 1000 μm. The scaffold may have an average width in a range of about 10 μm to about 100 μm.

A scaffold of the plurality of scaffolds may comprise a fiber scaffold. The fiber scaffold may be formed from polyvinylalcohol, polyacrylamide, polyvinylpyrrolidone, poly(2-hydroxyethyl methacrylate), polystyrene, polypropylene, polygalacturonic acid, and/or combinations thereof. The fiber scaffold may comprise a plurality of fibers. Each fiber in the plurality of fibers may be anchored to a bottom portion of each well. Anchored ends of individual fibers may be distanced about 100 μm to about 200 μm apart from one another in each well.

In an aspect, a scaffold of the plurality of scaffolds may comprise an artificial vascular scaffold. The artificial vascular scaffold may comprise a hydrogel. The artificial vascular scaffold may comprise a hollow fiber. The artificial vascular scaffold may comprise a plurality of hollow fibers. Individual hollow fibers may be anchored to the bottom of a well about 100 μm to about 200 μm from one another. The hollow fiber may be formed from a non-ionic polymer. The non-ionic polymer may comprise polyvinylalcohol, polyacrylamide, polyvinylpyrrolidone, poly(2-hydroxyethyl methacrylate), polystyrene, polypropylene, polygalacturonic acid, and/or combinations thereof. The hollow fiber further may comprise a hydrogel coating.

In an aspect, a method of culturing three-dimensional (3D) cell cultures is provided. The method comprises seeding cells in a cell culture device according to any of the aspects described herein, wherein the cells attach to the cell adherent surface of the scaffold disposed within the cell culture device; and culturing the cells into a 3D cell culture by adding cell culture medium to the cell culture device to provide nutrients and oxygen, wherein the cells remain attached to the scaffold during addition or exchange of cell culture medium; and optionally digesting the scaffold. The method may further comprise imaging 3D cell cultures attached to the scaffolds of the cell culture device.

In an aspect, an interconnected cell culture device is provided. The interconnected cell culture device comprises a multi-well cell culture plate comprising a plurality of wells, each well comprising a top, a bottom, and a sidewall disposed between the top and the bottom, wherein each well is configured with an interior surface comprising a cell non-adherent surface; and a plurality of hydrogel scaffolds disposed in the multi-well cell culture plate, the plurality of hydrogel scaffolds comprising hydrogel fibers of differing lengths, wherein opposite ends of a hydrogel fiber are disposed in different wells within the multi-well cell culture plate to create interconnected wells. The bottom may comprise a hemispherical shape. The hydrogel fibers may have lengths in a range of about 100 μm to about 100 mm. The hydrogel fibers may have average widths of about 10 μm. Each hydrogel fiber may comprise a cell-adherent surface. The hydrogel fibers may be formed of extracelluar matrix (ECM) proteins, decellularized tissue ECM scaffolds, ECM peptide binding sequences, crosslinked polymers, and/or combinations thereof. The hydrogel scaffolds may be unanchored or free-floating within the wells. The bottom may comprise a plurality of microcavities. Opposite ends of hydrogel fibers may be disposed in different microcavities to create interconnected microcavities.

In an aspect, a method of forming an interconnected cell culture device is provided. The method comprises seeding a cell culture device with cells, the cell culture device comprising a multi-well cell culture plate comprising a plurality of wells, each well comprising a top, a bottom, and a sidewall disposed between the top and the bottom and having an interior surface comprising an ultra-low attachment surface; seeding the cell culture device with a plurality of hydrogel scaffolds, the hydrogel scaffolds comprising a plurality of hydrogel fibers, wherein opposite ends of a hydrogel fiber are disposed in different wells within the multi-well cell culture plate to create interconnected wells; and providing cell culture medium to provide nutrients and oxygen for cell growth and formation of three-dimensional (3D) cell cultures. The bottom may comprise a hemispherical shape. The bottom may comprise a plurality of microcavities.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

It will be appreciated that the various disclosed embodiments may involve particular features, elements, or steps that are described in connection with that particular embodiment. It will also be appreciated that a particular feature, element, or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "an opening" includes examples having two or more such "openings" unless the context clearly indicates otherwise.

All scientific and technical terms used herein have meanings commonly used in the art unless otherwise specified. The definitions provided herein are to facilitate understanding of certain terms used frequently herein and are not meant to limit the scope of the present disclosure.

As used herein, "have," "having," "include," "including," "comprise," "comprising," or the like are used in their open-ended sense, and generally mean "including, but not limited to."

Ranges may be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All numerical values expressed herein are to be interpreted as including "about," whether or not so stated, unless expressly indicated otherwise. It is further understood, however, that each numerical value recited is precisely contemplated as well, regardless of whether it is expressed as "about" that value. Thus, "a dimension less than 10 mm" and "a dimension less than about 10 mm" both include embodiments of "a dimension less than about 10 mm" as well as "a dimension less than 10 mm."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising A+B+C include embodiments where a method consists of A+B+C, and embodiments where a method consists essentially of A+B+C.

Although multiple embodiments of the present disclosure have been described in the Detailed Description, it should be understood that the disclosure is not limited to the disclosed embodiments, but is capable of numerous rearrangements, modifications and substitutions without departing from the disclosure as set forth and defined by the following claims.

What is claimed is:

1. A cell culture device comprising: a multi-well cell culture plate comprising a plurality of wells, each well comprising a top aperture, a bottom, and a sidewall disposed between the top and the bottom, wherein each well is configured with an interior surface comprising a cell non-adherent surface; and a plurality of scaffolds disposed within the plurality of wells of the multi-well cell culture plate, wherein at least one scaffold is disposed in each well and each scaffold comprising a cell-adherent surface; wherein the bottom comprises a plurality of microcavities; and wherein a scaffold is anchored to a bottom portion of each microcavity of the plurality of microcavities.

2. The device of claim 1, wherein the bottom comprises a hemispherical shape.

3. The device of claim 1, wherein at least one end of the scaffold is anchored to a bottom portion of each well.

4. The device of claim 1, wherein the scaffold has an average length in a range of 100 pm to 1000 pm.

5. The device of claim 1, wherein the scaffold has an average width in a range of 10 pm to 100 pm.

6. The device of claim 1, wherein a scaffold of the plurality of scaffolds comprises a fiber scaffold.

7. The device of claim 6, wherein the fiber scaffold is formed from polyvinylalcohol, polyacrylamide, polyvinylpyrrolidone, poly(2-hydroxyethyl methacrylate), polystyrene, polypropylene, polygalacturonic acid, and/or combinations thereof.

8. The device of claim 7, wherein the fiber scaffold comprises a plurality of fibers.

9. The device of claim 8, wherein each fiber in the plurality of fibers is anchored to a bottom portion of each well.

10. The device of claim 9, wherein anchored ends of individual fibers are distanced 100 μm to 200 μm apart from one another in each well.

11. The device of claim 1, wherein a scaffold of the plurality of scaffolds comprises an artificial vascular scaffold.

12. The device of claim 11, wherein the artificial vascular scaffold comprises a hollow fiber.

13. The device of claim 11, wherein the artificial vascular scaffold comprises a plurality of hollow fibers.

14. The device of claim 13, wherein individual hollow fibers are anchored to the bottom of a well 100 μm to 200 μm from one another.

15. The device of claim 12, wherein the hollow fiber is formed from a non-ionic polymer.

16. The device of claim 15, wherein the non-ionic polymer comprises polyvinylalcohol, polyacrylamide, polyvinylpyrrolidone, poly(2-hydroxyethyl methacrylate), polystyrene, polypropylene, or polygalacturonic acid.

17. The device of claim 12, wherein the hollow fiber further comprises a hydrogel coating.

18. The device of claim 11, wherein the artificial vascular scaffold comprises a hydrogel.

19. A method of culturing three-dimensional (3D) cell cultures, the method comprising:

seeding cells in a cell culture device according to claim 1, wherein the cells attach to the cell adherent surface of each scaffold disposed within the cell culture device; and culturing the cells into a 3D cell culture by adding cell culture medium to the cell culture device to provide nutrients and oxygen, wherein the cells remain attached to each scaffold during addition or exchange of cell culture medium; and optionally digesting each of the plurality of scaffolds.

20. The method of claim 19, further comprising imaging 3D cell cultures attached to each of the plurality of scaffolds of the cell culture device.

* * * * *